(12) United States Patent
Hartlaub

(10) Patent No.: US 7,505,869 B2
(45) Date of Patent: Mar. 17, 2009

(54) NON-CONFORMANCE MONITORING AND CONTROL TECHNIQUES FOR AN IMPLANTABLE MEDICAL DEVICE

(75) Inventor: Jerome T. Hartlaub, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 37 days.

(21) Appl. No.: 11/358,607

(22) Filed: Feb. 21, 2006

(65) Prior Publication Data

US 2006/0161376 A1 Jul. 20, 2006

Related U.S. Application Data

(62) Division of application No. 10/001,357, filed on Oct. 31, 2001, now Pat. No. 7,054,782.

(60) Provisional application No. 60/259,008, filed on Dec. 29, 2000.

(51) Int. Cl.
*G01L 19/00* (2006.01)
(52) U.S. Cl. ..................... 702/182
(58) Field of Classification Search ............... 702/182
See application file for complete search history.

(56) References Cited

U.S. PATENT DOCUMENTS

| 4,731,051 A | 3/1988 | Fischell |
| 4,766,542 A | 8/1988 | Pilarczyk |
| 4,784,645 A | 11/1988 | Fischell |
| 4,810,243 A | 3/1989 | Howson |
| 4,871,351 A | 10/1989 | Feingold |
| 5,188,106 A | 2/1993 | Nappholz |
| 5,190,522 A | 3/1993 | Wojcicki |
| 5,389,078 A | 2/1995 | Zalesky |
| 5,417,717 A | 5/1995 | Salo |
| 5,950,630 A | 9/1999 | Portwood |
| 5,970,466 A | 10/1999 | Detjen |
| 6,003,006 A | 12/1999 | Colella |
| 6,201,993 B1 | 3/2001 | Kruse |
| 6,234,973 B1 | 5/2001 | Meador |
| 6,385,593 B2 * | 5/2002 | Linberg ............... 705/28 |
| 6,558,320 B1 | 5/2003 | Causey |
| 6,589,205 B1 * | 7/2003 | Meadows ............. 604/67 |
| 2007/0168222 A1 * | 7/2007 | Hoyme et al. ......... 705/2 |

FOREIGN PATENT DOCUMENTS

WO WO8401719 5/1984

(Continued)

*Primary Examiner*—Tung S Lau
(74) *Attorney, Agent, or Firm*—Banner & Witcoff, Ltd.

(57) ABSTRACT

Disclosed is a method and apparatus for determining whether an implantable drug delivery device is conforming to the performance requirements of the device or the needs of the patient. The system includes an implantable drug delivery device having stored therein at least one drug, a nonconformance monitor module monitoring pump parameters, an external programmer in telemetric communication with the implantable drug delivery device and having a nonconformance management module for determining whether the device is conforming to performance requirements, and to determine what action should be taken if non-conformance is determined. If the nonconformance management module identifies nonconformance, it determines what action should be taken for the particular non-conformance. The nonconformance management module will either invoke a pump programming change, or schedule and appointment or notify the patient that a non-programming change should be made.

15 Claims, 8 Drawing Sheets

FOREIGN PATENT DOCUMENTS

| | | |
|---|---|---|
| WO | WO9424929 | 11/1994 |
| WO | WO9613790 | 5/1996 |
| WO | WO9910029 | 3/1999 |
| WO | WO9944167 | 9/1999 |
| WO | WO0047108 | 8/2000 |
| WO | WO0072181 | 11/2000 |
| WO | WO0148676 | 7/2001 |
| WO | WO0152935 | 7/2001 |

* cited by examiner

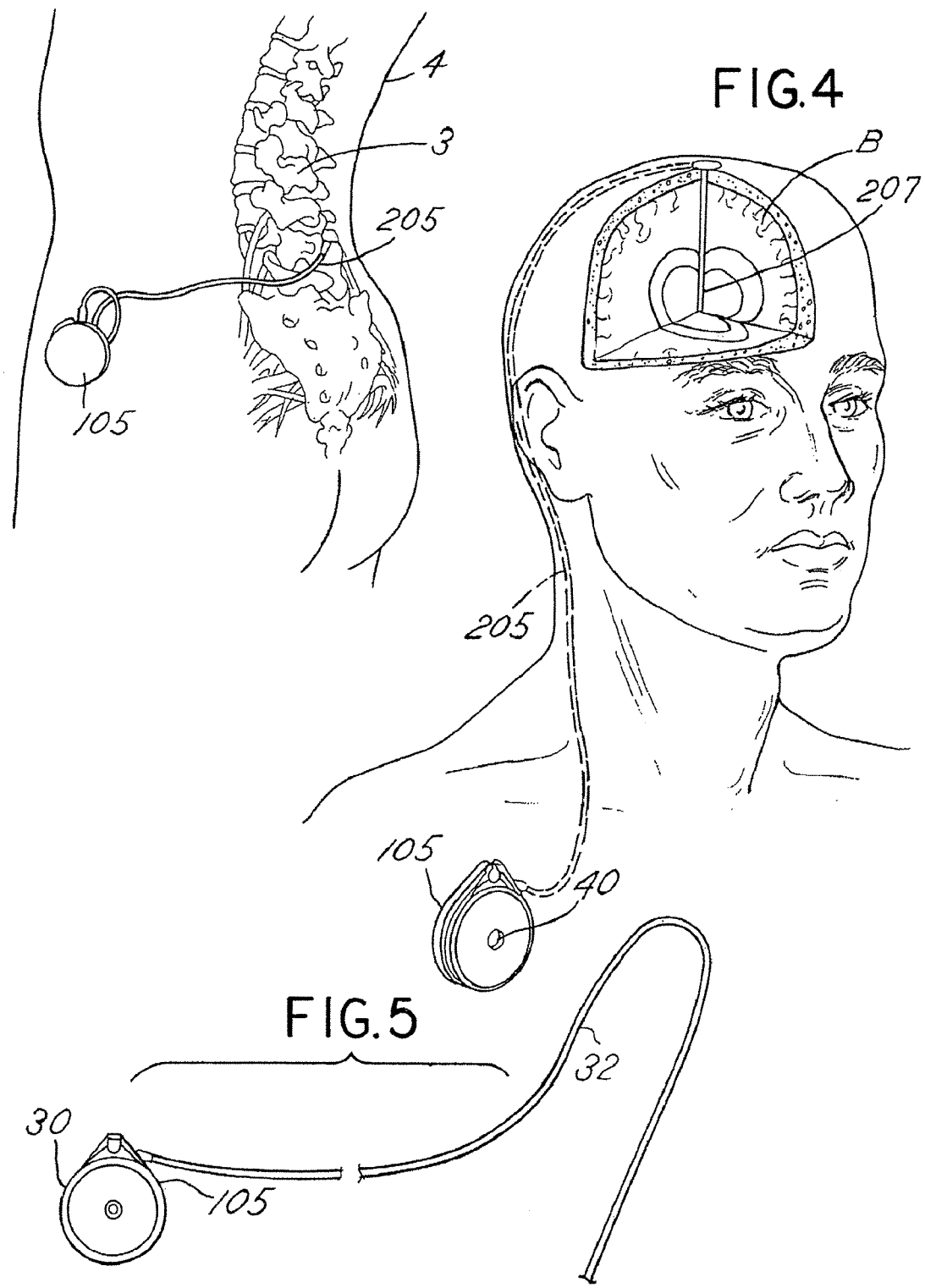

NON-CONFORMANCE MONITORING AND CONTROL TECHNIQUES FOR AN IMPLANTABLE MEDICAL DEVICE

This application is a divisional application of U.S. application Ser. No. 10/001,357 filed Oct. 31, 2001, which claims the benefit of U.S. Provisional Application No. 60/259,008, filed Dec. 29, 2000. The prior applications are hereby incorporated by reference in their entireties.

This patent application is related to the following patent applications, each of which having the same named inventor as the present application:

a. U.S. patent application Ser. No. 10/000,701, entitled "Drug Management Techniques for an Implantable Medical Device," based on U.S. Provisional Application No. 60/259,115, filed Dec. 29, 2000;

b. U.S. patent application Ser. No. 10/002,669, entitled "Patient Scheduling Techniques for an Implantable Medical Device," based on U.S. Provisional Application No. 60/259,022, filed Dec. 29, 2000; and c. U.S. Pat. No. 6,799,149 issued Sep. 28, 2004, entitled "Therapy Management Techniques for an Implantable Medical Device," based on U.S. Provisional Application No. 60/259,116, filed Dec. 29, 2000.

Each of these related patent applications are incorporated herein by reference in their entireties.

FIELD OF THE INVENTION

This invention relates to implantable drug delivery devices such as implantable drug delivery devices, and more particularly relates to automated non-compliance monitoring and control systems and methods for implantable drug delivery devices.

BACKGROUND OF THE INVENTION

The medical device industry produces a wide variety of electronic and mechanical devices suitable for use outside and inside the body for treating patient disease conditions. Devices used outside the body are termed external while devices used inside the body are termed implantable and include therapeutic substance infusion devices such as implantable drug pumps. Clinicians use medical devices alone or in combination with therapeutic substance therapies and surgery to treat patient medical conditions. For some medical conditions, medical devices provide the best, and sometimes the only, therapy to restore an individual to a more healthful condition and a fuller life. Implantable therapeutic substance infusion devices can be used to treat conditions such as pain, spasticity, cancer, and a wide variety of other medical conditions.

Implantable medical devices have important advantages over other forms of therapeutic substance administration. For example, oral administration is often not workable because the systemic dose of the substance needed to achieve the therapeutic dose at the target sight may be too large for the patient to tolerate without very adverse side effects. Also, some substances simply will not be absorbed in the gut adequately for a therapeutic dose to reach the target sight. Moreover, substances that are not lipid soluble may not cross the blood-brain barrier adequately if needed in the brain. In addition, infusion of substances from outside the body requires a transcutaneous catheter, which results in other risks such as infection or catheter dislodgement. Further, implantable medical devices avoid the problem of patient noncompliance, namely the patient failing to take the prescribed drug or therapy as instructed.

Implantable medical devices are often used in conjunction with various computer and telecommunication systems and components. Information obtained by the implantable medical device may be stored and subsequently transmitted to a physician or patient caregiver or a database on demand or automatically. Many ways of using the information are known including decision making to provide optimum medical care to the person with the medical condition.

An implantable therapeutic substance infusion device such as an implantable drug delivery device is implanted by a clinician into a patient at a location appropriate for the therapy that interferes as little as practicable with normal patient activity. This location is typically a subcutaneous region in the lower abdomen. The proximal or near end of the infusion catheter is connected to the drug pump infusion outlet. The catheter is simply a flexible tube with a lumen typically running the length of the catheter. The distal or far end of the catheter is positioned to infuse a drug or drug combination to a target site in the patient. Target sights in the body included but are not limited to an internal cavity, any blood vessel, any organ, or other tissue in the body. The drug or other therapeutic substance flows from the pump via the lumen in the catheter at a programmed infusion rate to treat the disease condition. The pump typically includes an expansible reservoir for containing a refillable supply of drug. For example, U.S. Pat. No. 4,692,147 (Duggan) and U.S. Pat. No. 5,445,616 (Kratoska et al) disclose types of implantable pumps that can be used.

Examples of diseases that are treatable include spasticity and chronic intractable pain. To treat spasticity, the distal tip of the catheter is typically surgically positioned in the intrathecal space of the patient's spinal column. Drug flows out of the distal tip into the cerebral spinal fluid where it baths the spinal cord. By virtue of molecular action on nervous tissue in the spinal cord, the patient's spasticity symptoms are dramatically reduced and the patient becomes much more comfortable and competent. Pain patients are treated in much the same way.

The infusion rate of the drug pump is typically programmed to be variable over time. The rate is usually controlled by certain components in the pump. The controlled infusion rate is often further set by using an external device or programmer to transmit into the pump, instructions for the controlled infusion. The controlled infusion may be variable as time passes according to the needs of the patient. The instructions provided to the pump to control the infusion rate of the drug pump are typically determined by a medical person. In some cases the patient is able to provide the instructions to the pump via an external patient-programming device. In contrast, fixed rate pumps usually cannot be programmed and are only capable of constant infusion rate.

Once implanted within the patient's body, it is critical that the implanted device perform adequately to provide the necessary treatment therapy to the patient. It is possible, however, that the device does not quite perform as desired or as configured. There may be any number of reasons for this non-compliance of the device including for example, the implanted device may fail to operate, the catheter may be occluded or kinked, the system may be delivering an insufficient amount of drug, the device battery may be low, there may be air in the drug reservoir, the device motor may have failed, or there may be a low drug level.

The patient or physician may not necessarily know that the device is not performing as expected. The patient/physician may, for example, incorrectly diagnose that the treatment therapy is not working. Even if it is determined that the device is not performing as required, the physician may not know what specifically is causing the problem. As a result, the patient may have to endure another surgical procedure to repair or replace the device.

Even if it can be readily determine that the device is not performing as required, the physician must still meet with the patient to determine how to resolve the problem. The physician may have to contact the device manufacturer to help resolve the problem. Until the physician can properly treat the problem, the patient must endure a time period where he/she is receiving inadequate treatment therapy.

It is therefore desirable to provide a way to determine whether a device is not performing as required without requiring the patient to endure a surgical procedure. It is also desirable to provide a way to efficiently identify the cause of the device non-compliance and then to identify the best course of action to remedy the non-compliance.

BRIEF SUMMARY OF THE INVENTION

The present invention is an automated management control system for implantable drug delivery devices. In a preferred embodiment, the overall system generally includes an implantable drug delivery device, an external device having a nonconformance management module in bi-directional communication with the implantable device, a computing network coupled to the external programmer and various entities involved in the healthcare management of the patient. The nonconformance management module gathers data regarding the implantable drug delivery device to determine whether the device is conforming to performance requirements, and to determine what action should be taken if non-conformance is determined. The nonconformance management module receives as inputs, pump performance acquisition instructions, drug management data, patient performance requirements information, and pump manufacturer requirements information. Provided back to the implantable drug delivery device are pump performance acquisition instructions that provide information about the particular pump performance data information that needs to be gathered. Based on the inputs, if the nonconformance management module identifies nonconformance, it determines what action should be taken for the particular non-conformance. The nonconformance management module will either invoke a pump programming change, or schedule and appointment or notify the patient that a non-programming change should be made.

In alternative embodiments, the nonconformance management module may be implemented in other parts of the overall system for nonconformance management including, for example, in the implantable drug delivery device or on a server accessible over the computing network.

The objects, advantages novel features, and the further scope of applicability of the present invention will be set forth in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 3 illustrates a typical position in a patient of an implantable drug delivery device with a catheter implanted at or near a spinal cord.

FIG. 4 illustrates another typical position in a patient of an implantable drug delivery device with a catheter implanted at or near a brain.

FIG. 5 depicts the implantable drug delivery device.

DETAILED DESCRIPTION OF THE INVENTION

In accordance with the present invention, an implantable drug delivery device is equipped with automated management control capabilities. Although described in the context of implanted drug delivery devices, the present invention may also be implemented generally within implantable medical devices, including but not limited to, implantable electrical stimulation devices, combined drug delivery and stimulation devices, cardiac devices, and the like.

Although not required, the invention will be described in part in the general context of computer-executable instructions, such as program modules. Generally, program modules include routines, programs, objects, scripts, components, data structures, etc. that perform particular tasks or implement particular abstract data types. Program modules may be part of a single software program, may be implemented as separate software programs, or may be part of hardwired devices having various electronic components for carrying out the desired functionality.

Figure 1:
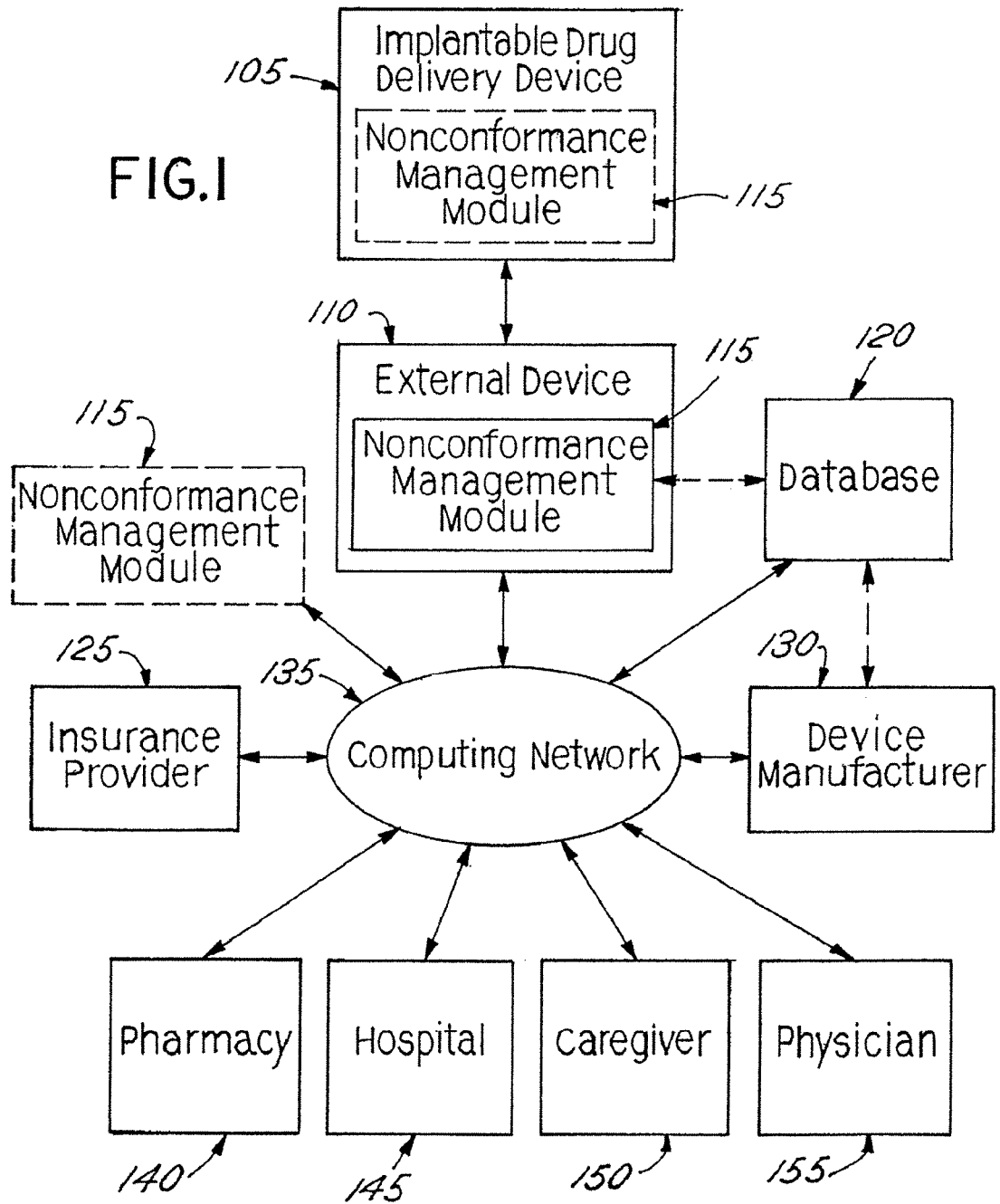
FIG. 1 is a schematic block diagram of an overall system for nonconformance management of an implantable drug delivery device in accordance with a preferred embodiment of the present invention.

FIG. 1 is a schematic block diagram of an overall system for nonconformance management of an implantable drug delivery device in accordance with a preferred embodiment of the present invention. The overall system generally includes an implantable drug delivery device 105 implantable within a patient, an external device or programmer 110 having a nonconformance management module 115 in accordance with a preferred embodiment of the present invention, a database 120, and a computing network 135 such as the Internet coupled to various entities involved in the healthcare management of the patient. Such entities may include, for example, an insurance provider 125, a pharmacy 140, a hospital 145, a caregiver 150, a physician 155, and/or a device manufacture 130. In alternative embodiments, the nonconformance management module 115 may be implemented in other parts of the overall system for nonconformance management including, for example, in the implantable drug delivery device 105, or on a server accessible over the computing network 135. Further details of the nonconformance management module are discussed in further detail herein. The implantable drug delivery device 105 is coupled to be in bi-directional communication with the external device 110 via telemetry. The external device 110 may be any computing device capable of communicating with the implantable drug delivery device 105, including for example, a physician programmer, a patient programmer, a screening device, a data acquisition device and the like. The bi-directional communications may be of any type of telemetry including RF.

The external device 110 is preferably coupled to the computing network 135 for communicating with various healthcare entities essential to the management of the treatment therapy of the patient. Also coupled to the network 135 and in communication with the external device 110 is the database 120 storing nonconformance management information relating to the patient. The computing network 135 may be, for example, a public network such as the Internet, an intranet, an extranet, or a private network. The computing network 135 enables the external device 110 to communicate with the various healthcare entities and the database 120.

The external device 110 may be coupled to the computing network 135 either directly through a modem or may be networked to a personal computer that is coupled to the computing network 135 through known techniques. The various other entities 125, 130, 140-155 are preferably coupled to the computing network 135 via a general-purpose computing device. Each of these entities 125, 130, 140-155 also preferably includes a user interface including, for example, a graphical user interface. The computing devices used by these entities preferably have installed therein a software application that communicates with the nonconformance management module to perform the various scheduling functions to be performed.

Figure 2:
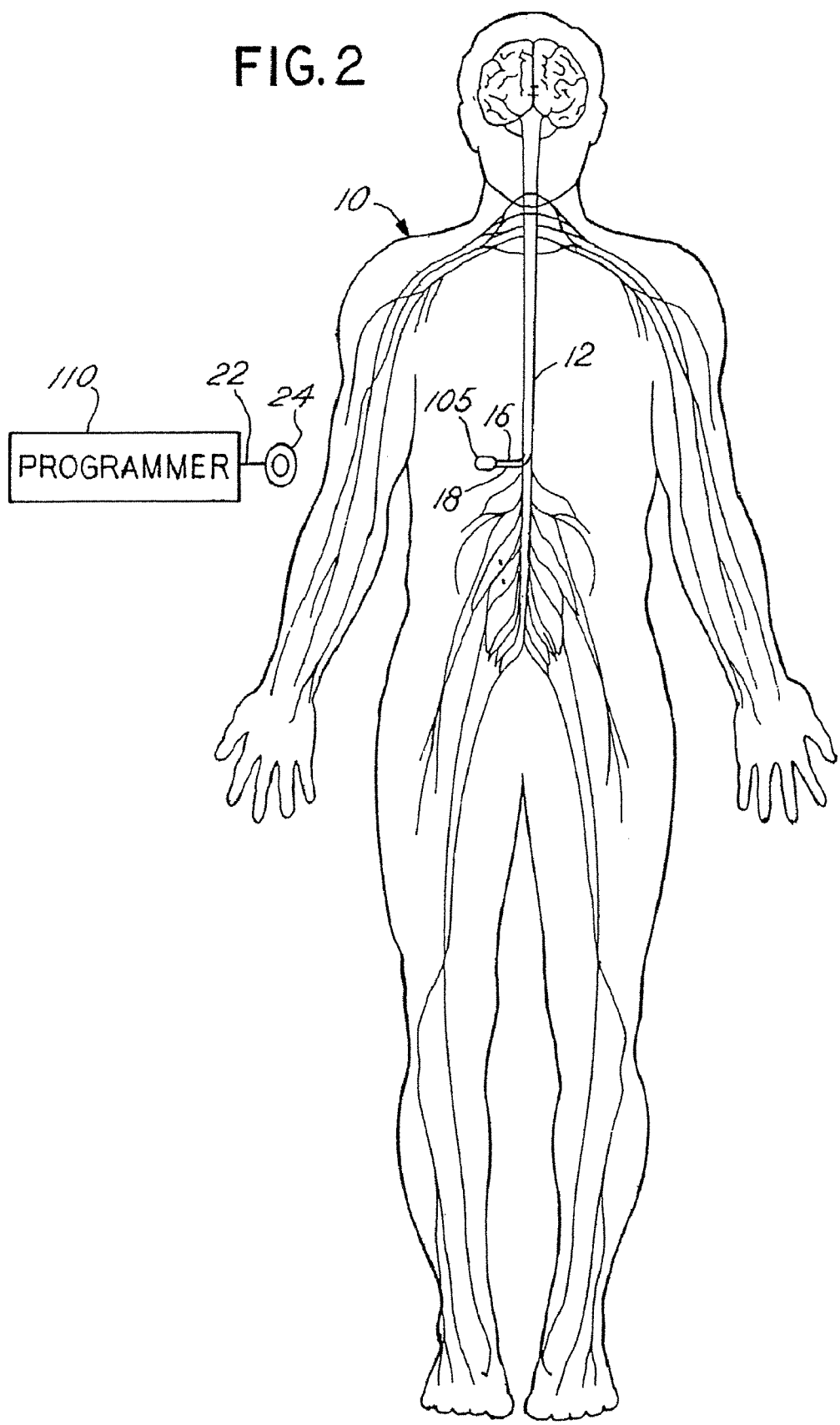
FIG. 2 is a diagrammatic view of a drug delivery device for use with the present invention as implanted within a patient.

As discussed, implantable drug delivery devices are generally known in the art. U.S. Pat. No. 4,692,147 (Duggan) and U.S. Pat. No. 5,445,616 (Kratoska et al), for example, illustrate the general features of these devices. FIG. 2 is a diagrammatic illustration of an exemplary implantable drug delivery device 105 for use with the present invention. The system includes the device 105 that may be implanted below the skin of a patient 10 in the abdomen or any other location of the body. The device 105 is typically a pump that delivers drug to a catheter 16/18 that is positioned to deliver the drug to specific infusion sites within the patient's body (in this case, the spinal cord 12). The distal end of the catheter 16/18 terminates in a cylindrical hollow tube having a distal end implanted into a portion of the body by conventional surgical techniques. The catheter 16/18 is joined to the implanted device 105 in the manner shown, and may be secured to the device 105 by, for example, screwing the catheter 16/18 onto a catheter port of the device 105.

The implantable system 105 may include one or more sensors to provide closed-loop feedback control of the drug delivery system to provide enhanced results. Sensors can be used with a closed loop feedback system to automatically determine the level of treatment therapy necessary to alleviate the symptoms of the disorder being treated. The sensor is attached to or implanted into a portion of a patient's body suitable for detecting symptoms of the disorder being treated, such as a motor response or motor behavior. The sensor is adapted to sense an attribute of the symptom to be controlled or an important related symptom. For movement disorders that result in abnormal movement of an arm of the patient, such as an arm, the sensor may be a motion detector implanted in the arm. For example, the sensor may sense three-dimensional or two-dimensional motion (linear rotational or joint motion), such as by an accelerometer. One such sensor suitable for use with the present invention is described in U.S. Pat. No. 5,293,879 (Vonk). The sensor also may be placed in the implantable drug delivery device, for example, to sense drug levels. Those skilled in the art will appreciate that any type of sensor may be utilized with the present invention. The output of the sensor may be coupled by a cable or via telemetry to the input of an analog to digital converter within the implantable drug delivery device. Alternatively, the output of an external sensor would communicate with the implantable drug delivery device through a telemetry downlink.

The implantable drug delivery device 105 can be used for a wide variety of therapies to treat medical conditions (also known as medical indications) such as pain, spasticity, cancer, and many other medical conditions. The implantable drug delivery device 105 is typically implanted by a clinician, such as a surgeon, using a sterile surgical procedure performed under local, regional, or general anesthesia. Before implanting the therapeutic substance infusion device, a catheter is typically implanted with the distal end position at the desired therapeutic substance infusion site and the proximal end tunneled to the location where the therapeutic substance infusion device is to be implanted. The implantable therapeutic substance infusion device is generally implanted subcutaneously about 2.5 cm (1.0 inch) beneath the skin where there is sufficient subcutaneous tissue to support the implanted system. As one example, FIG. 3 illustrates the implantable drug delivery device 105 coupled to catheter 205, both of which are under the surface of the skin 4. The catheter 205 is positioned with its distal tip in the intrathecal space of the spinal column 3. As another example, FIG. 4 shows the implantable drug delivery device 105 for infusion of drug into to brain B. The device 105 is coupled to catheter 205 with a distal end terminating within the brain B. FIG. 5 illustrates the various components of the implantable drug delivery device 105 that are implanted within the patient 10.

Once the therapeutic substance infusion device is subcutaneously implanted into the patient, the incision can be sutured closed and the therapeutic substance infusion device can begin operation. The implantable drug delivery device 105 operates to infuse a therapeutic substance at a programmed rate into a patient. The therapeutic substance is a product or substance intended to have a therapeutic effect such as pharmaceutical compositions, genetic materials, biologics, and other substances. Pharmaceutical compositions are chemical formulations intended to have a therapeutic effect such as intrathecal antispasmodics (e.g., balcofen), pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances are substances intended to have a therapeutic effect yet are not easily classified such as saline solution, fluoroscopy agents, and the like. As used herein, the term drug shall refer generally to any therapeutic substance.

The therapeutic substance can be replenished in some embodiments of the implanted therapeutic substance infusion device by inserting a non-coring needle connected to a syringe filled with therapeutic substance through the patient's skin into a septum and into a reservoir in the therapeutic substance infusion device to fill the implanted device reservoir. Refill kits are available which include the drug and all other necessary equipment needed for the medical attendant to refill the pump.

A therapeutic substance bolus can be administered by a clinician, in some embodiments, by inserting a non-coring needle connected to a syringe into a catheter access port. This procedure can be used for several other reasons including reopening the catheter if it becomes occluded or to withdraw a sample of cerebral spinal fluid for investigative purposes.

Figure 6:
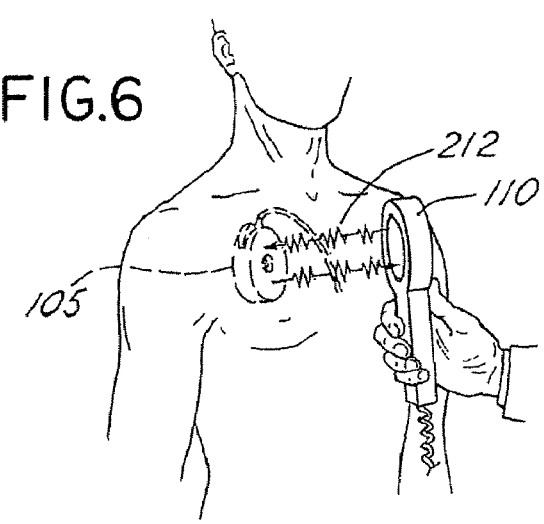
FIG. 6 shows an implantable pump communicating via telemetry with an external handheld programming device.

FIG. 6 illustrates a typical pump programming technique. An external device, a handheld programming device 110 in this embodiment, transmits and receives radio frequency signals 212 to and from the implantable drug delivery device 105. The radio frequency signals 212 sent to the pump, often called the downlink signal, contain the programming instructions needed by the implantable drug delivery device 105 for it to correctly infuse a drug into the patient from its drug reservoir. Many other types of information may be sent to the pump including requests for information residing in the pump in accordance with the present invention (discussed herein).

The implantable drug delivery device 105 may continuously or periodically store various types of information including, for example without limitation, pump diagnostics, drug delivery information, batter life, etc. Further, the implantable drug delivery device 105 may receive information from various sensors inside the pump or information from sensors integral with the catheter, thereby obtaining physiological information about the patient. Even further, the implantable drug delivery device 105 may store historical data about the drug infusing profile, patient requests for more drug or other such information.

Such information stored in the pump may be valuable to the treating physician and/or the medical device supplier and can be retrieved from the pump. In particular, the information stored in the implantable drug delivery device 105 may be retrieved in response to a request by the pump from the programming device 110. After the request is received and processed in the implantable drug delivery device 105, the implantable drug delivery device 105 prepares the requested information and sends it to the programming device 110, sometimes called uplink data. The pump information received by the programming device 110 is processed and converted to intelligible data for clinical or technical use. This intelligible data can be used for many purposes including management of the pump performance, management of the patient therapy, and/or other medical or record-keeping purposes.

Figure 7:
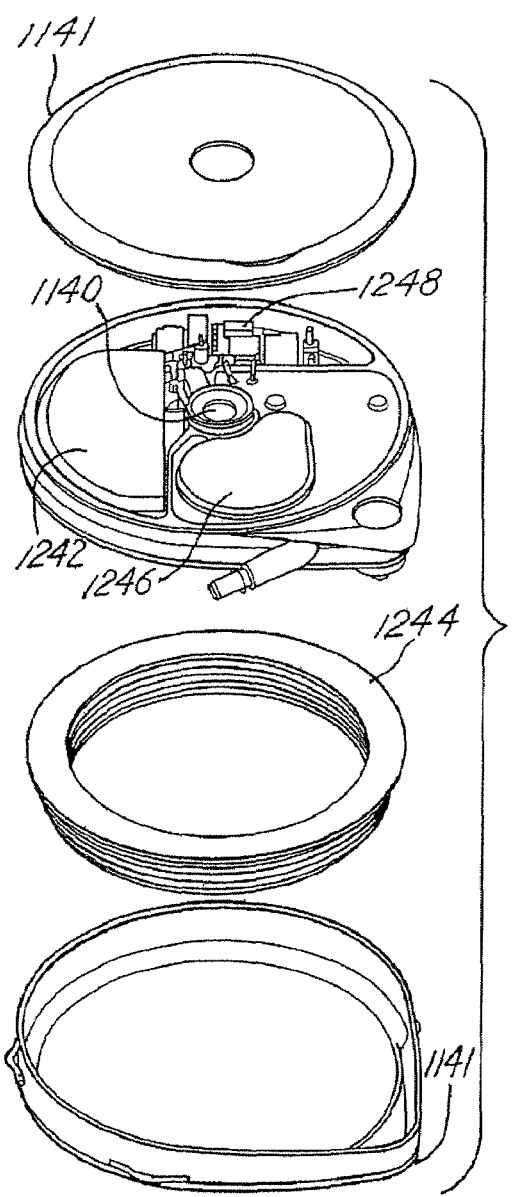
FIG. 7 is a diagrammatic view of an exemplary implantable drug delivery device for use with the present invention depicting the various layered components of the device.
Figure 8:
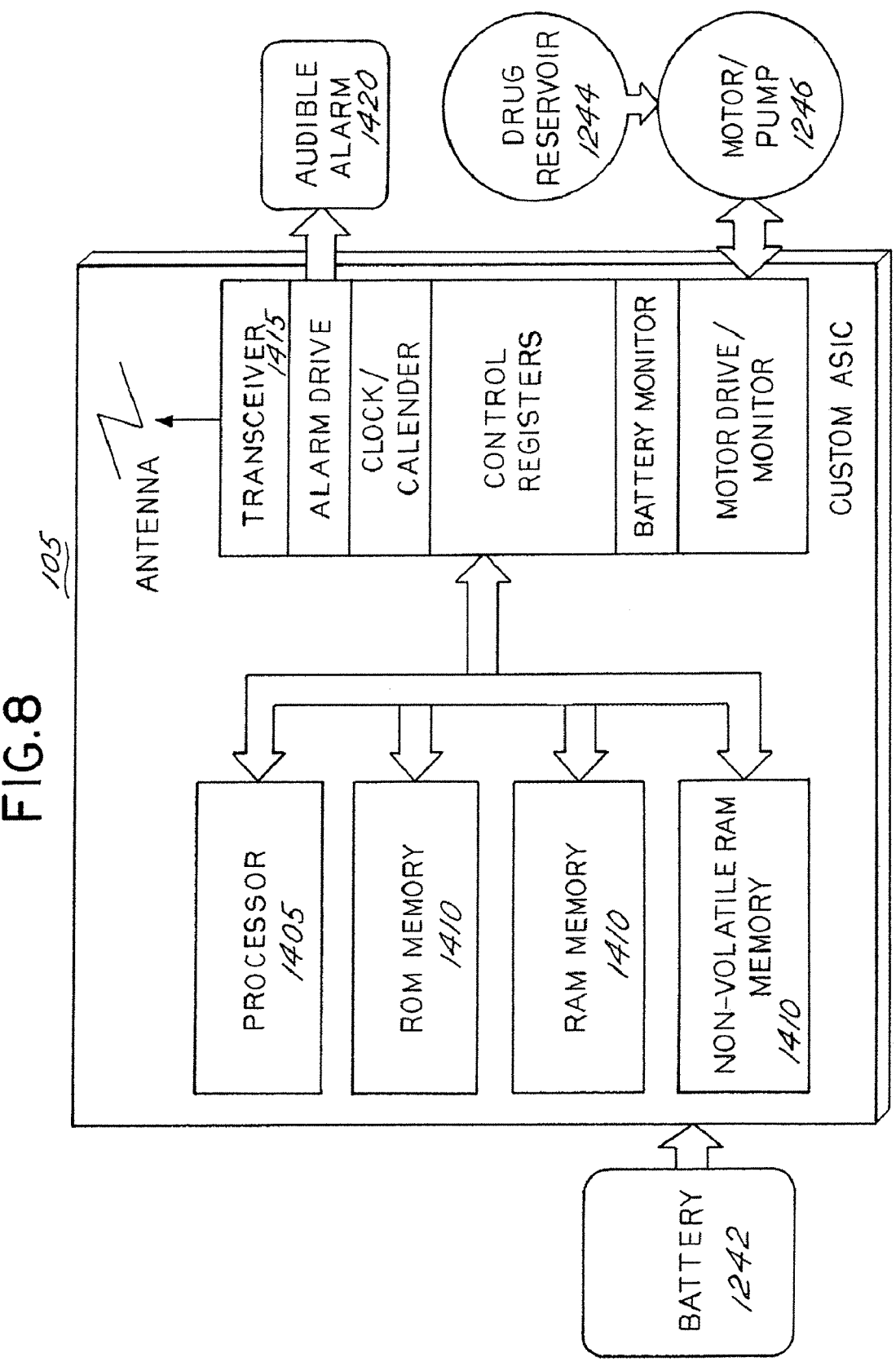
FIG. 8 shows a block diagram of an implantable drug delivery device embodiment for use with the present invention.

Referring back to the embodiment of the implantable drug delivery device, the present invention may be implemented for use any number of such devices. FIG. 7 show one such example of the implantable drug delivery device 105 and FIG. 8 shows a block diagram of the implantable drug delivery device 105. The implantable drug delivery device 105 generally comprises a housing 1141, a power source 1242, a therapeutic substance reservoir 1244, a therapeutic substance pump 1246, and electronics 1248. The housing 1141 is manufactured from a material that is biocompatible and hermetically sealed such as titanium, tantalum, stainless steel, plastic, ceramic, and the like. The power source 1242 is carried in the housing 1141. The power source 1242 is selected to operate the therapeutic substance pump 1246 and electronics 1248 such as a lithium ion (Li+) battery, capacitor, and the like.

The therapeutic substance reservoir 1244 is carried in the housing 1141. The therapeutic substance reservoir 1244 is configured for containing a therapeutic substance. The therapeutic substance reservoir 1244 may be refilled with therapeutic substance while implanted via port 1140. The therapeutic substance pump 1246 is carried in the housing 1141. The therapeutic substance pump 1246 is fluidly coupled to the therapeutic substance reservoir 1244 and electrically coupled to the power source 1242. The therapeutic substance pump 1246 is a pump that is sufficient for infusing therapeutic substance such as a piston pump, a peristaltic pump that can be found in the SynchroMed® Infusion System available from Medtronic, Inc., or a pump powered by a stepper motor, an AC motor, a DC motor, an electrostatic diaphragm, a piezoelectric diaphragm, a piezoelectric motor, a solenoid, a shape memory alloy, and the like.

The electronics 1248 are carried in the housing 1141 and coupled to the therapeutic substance pump 1246 and the power source 1242. The electronics 1248 include a processor 1405, memory 1410, an infusion program in memory, and transceiver circuitry 1415. The processor 1405 can be an Application Specific Integrated Circuit (ASIC) state machine, a gate array, controller, and the like. The electronics 1248 are configured to control the infusion rate of the therapeutic substance pump 1246 and can be configured to operate many other features such as patient alarms 1420 and the like. The infusion program resides in memory and is capable of being modified once the implantable drug deliver device is implanted. The transceiver circuitry 1415 is coupled to the processor 1405 for externally receiving and transmitting therapeutic substance infusion device information.

As discussed, the present invention is implemented in part as computer-executable instructions, such as program modules. In a preferred embodiment as discussed herein, some of the features of the present invention are implemented within a nonconformance management module 115. The implantable device 105 would provide via telemetry the necessary information for the external device 110 to provide the nonconformance management functionality of the present invention. In the embodiment where the nonconformance management module 115 is within the implantable device 105, it may be found in the electronic module 1242 or 32.

Figure 9:
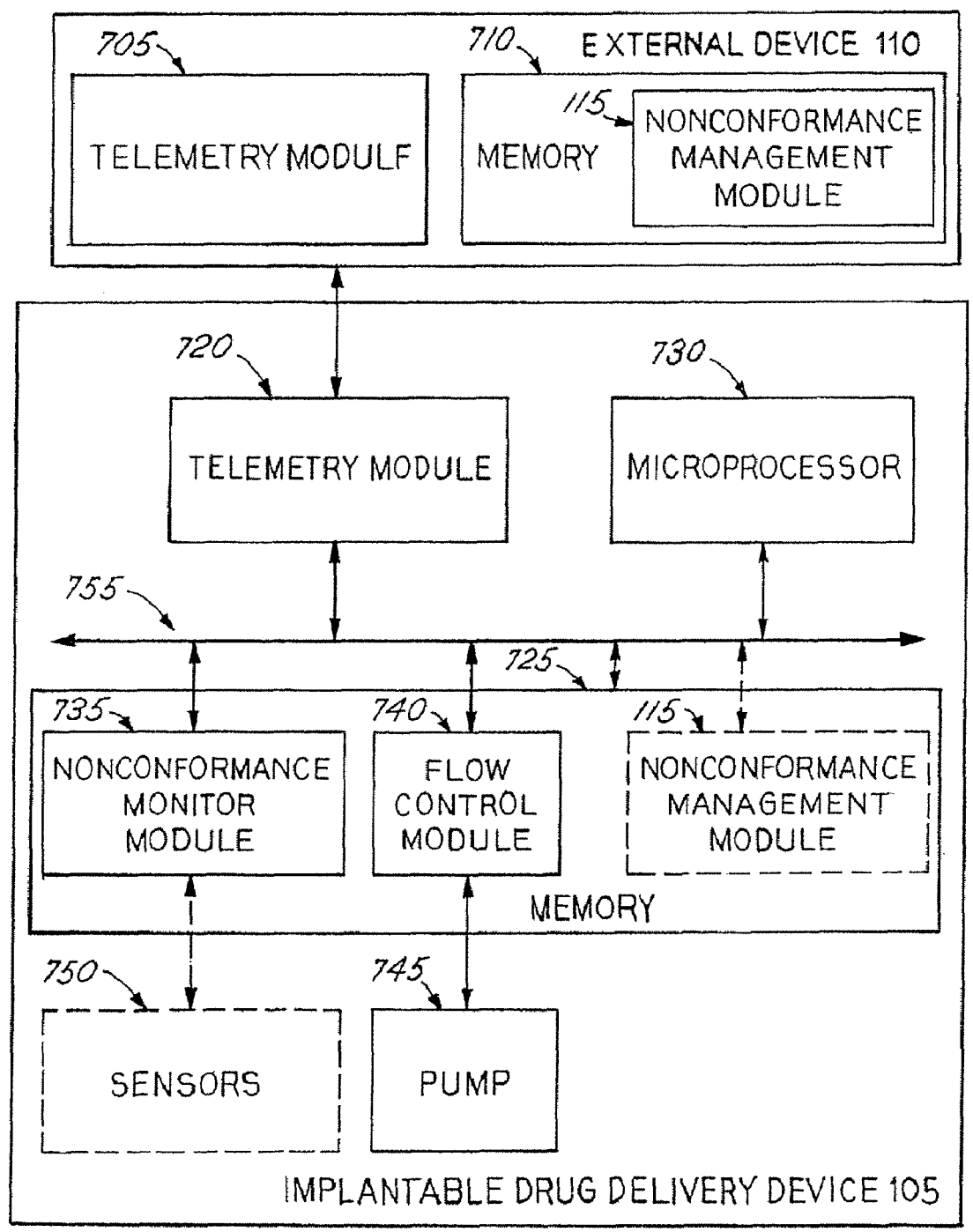
FIG. 9 is a schematic block diagram of the electronic modules of the implantable drug delivery device in accordance with a preferred embodiment of the present invention.

Referring to the schematic block diagram of FIG. 9, the implantable device 105 includes various electrical and software components including a microprocessor 730, a flow control module 740 for controlling the flow of drug from the reservoir to the infusion port, a telemetry module 720 for providing bi-directional communication between the implantable device 105 and the external device 110, a memory 725 for storing the various software modules for use with the present invention, a nonconformance monitor module 735, and (optionally) a nonconformance management module 115. The nonconformance monitor module 735 provides one or more pump performance parameters or data relating to the implantable device 105. The pump performance parameters monitored by the nonconformance monitor module 735 may include, for example and without limitation, pump reservoir pressure, fluid outlet pressure, propellant pressure, fluid flow rate, battery current drain, motor current drain, motor drive current profile, battery voltage, and physiologic sensor output level. These performance parameters may be determined, for example, by way of one or more sensors 750 that sense the various parameters.

The external device 110 generally includes a telemetry module 705 and a memory 710 for storing various software applications and modules for use with the present invention. Stored within the external device 110 is the nonconformance management module 115. The nonconformance management module 115 gathers data regarding the implantable device 105 to determine whether the pump is conforming to performance requirements, and to determine what action should be taken if non-conformance is determined.

Figure 10:
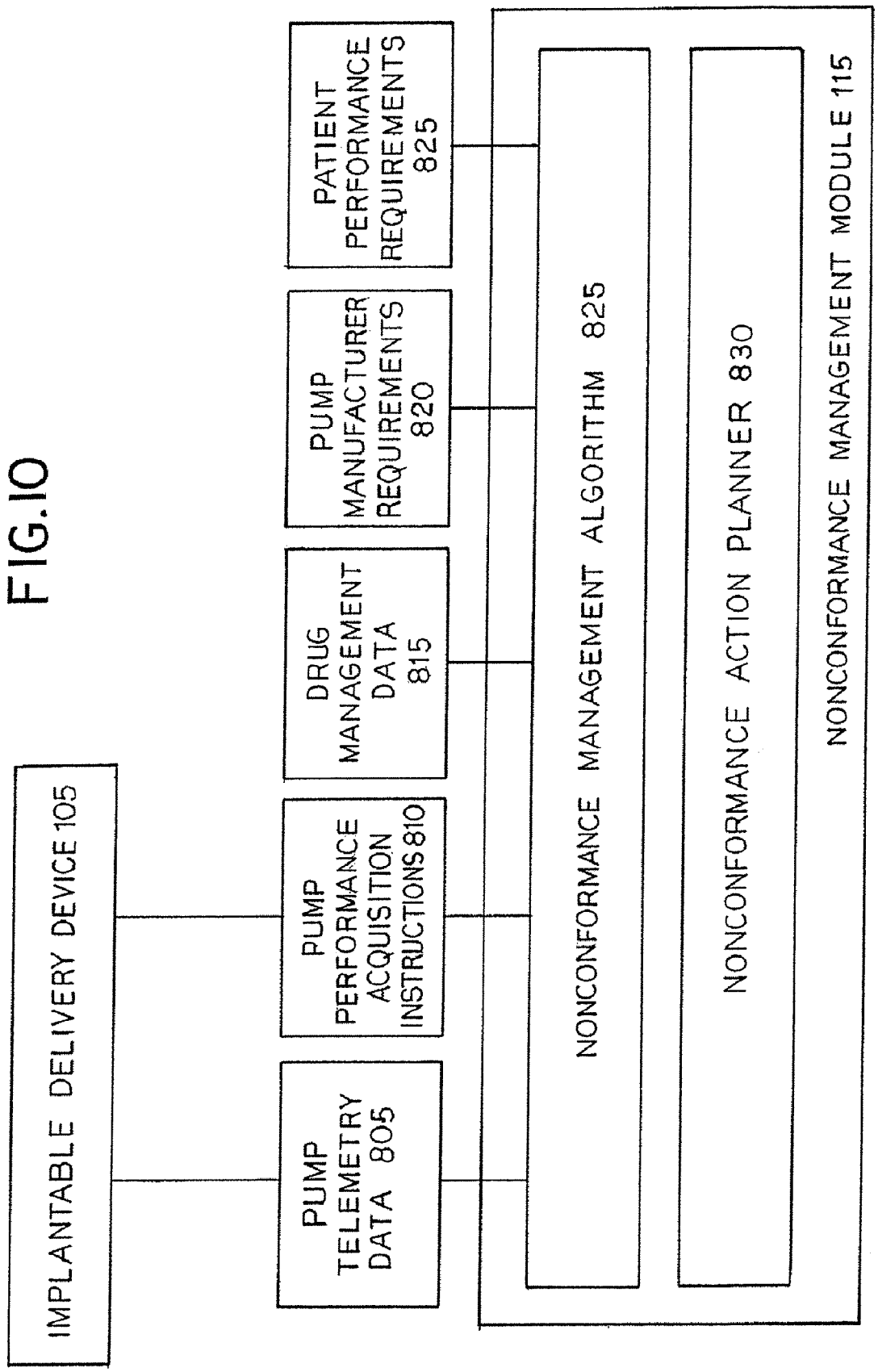
FIG. 10 is a schematic block diagram of the nonconformance management module of the implantable drug delivery device in accordance with a preferred embodiment of the present invention.

As shown in the block diagram of FIG. 10, the nonconformance management module 115 includes a nonconformance management algorithm 825 that gathers information including the pump performance data regarding the implantable device 105, drug management data 815, pump manufacturer requirements 820, and patient performance requirements 825. Provided back to the implantable drug delivery device 105 from the external device 110 are pump performance acquisition instructions 810 that provide information about the particular pump performance data information that needs to be gathered.

Figure 11:
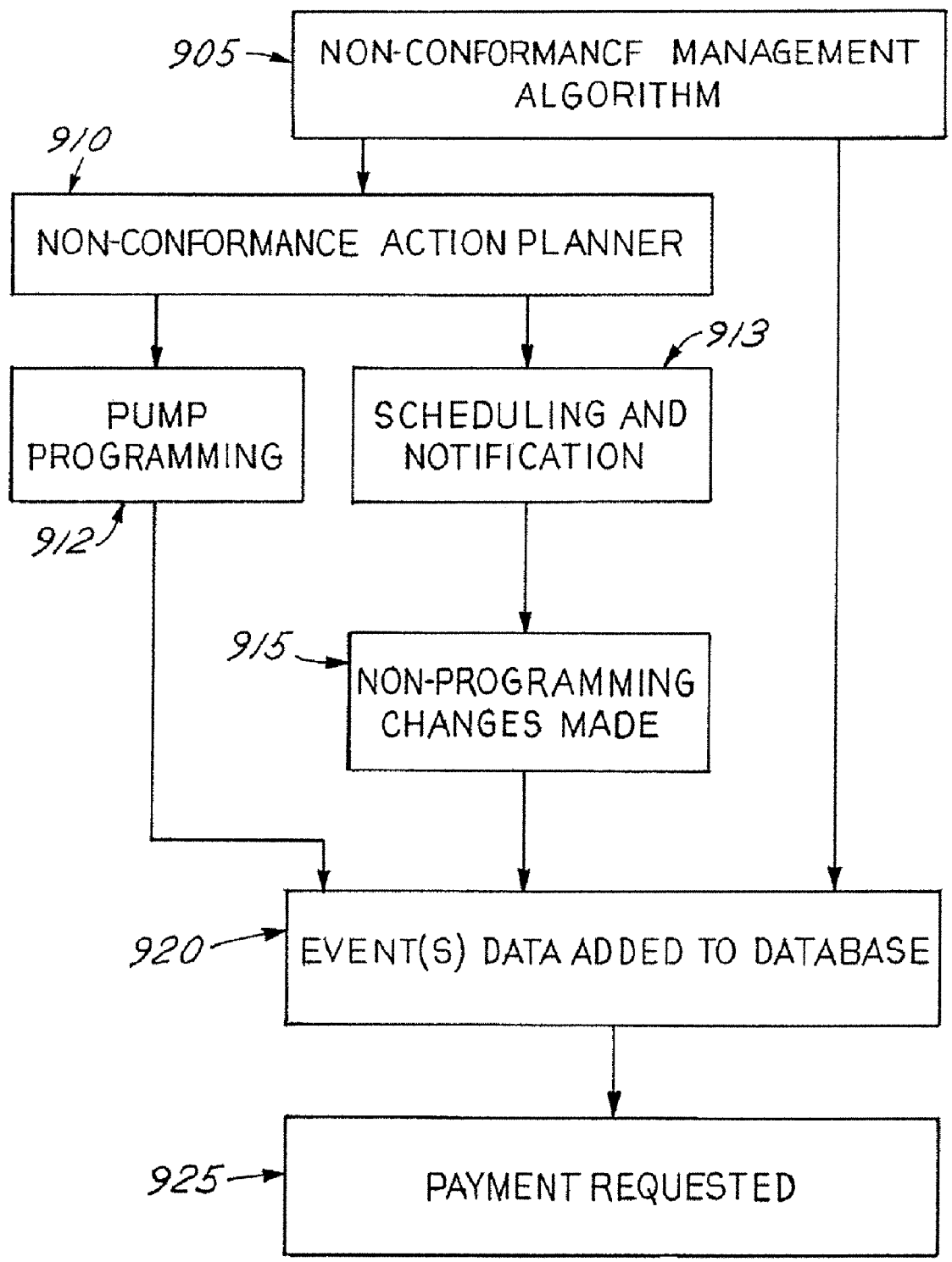
FIG. 11 is a flow chart depicting the process for determining whether nonconformance of the implantable drug delivery device has been detected in accordance with a preferred embodiment of the present invention.

FIG. 11 is a flow chart depicting the process for determining whether nonconformance of the implantable pump has been detected in accordance with a preferred embodiment of the present invention. At step 905, the nonconformance management algorithm 825 compares the pump performance data from the implantable device 105 with the drug management data 815, pump manufacturer requirements 820, and patient performance requirements 825 to determine whether the implantable pump 105 is conforming to performance requirements, and to determine what action should be taken if nonconformance is determined. For example, if a pressure measured inside the pump 105 at the output of the pumping mechanism is excessive, there is a possibility that the implanted catheter is kinked or blocked in some way, thereby causing the rate of drug infusion to be undesirably low. The nonconformance management algorithm 825 compares this pressure data to the manufacturer performance requirements for a particular level of pressure expected at this point in the pump mechanism. If the pump pressure is too high, at step 910, the nonconformance management algorithm 825 then communicates to the nonconformance action planner algorithm 830. Alternatively, if the pressure telemetered from the pump 105 is only intermittently high or doesn't supersede the performance requirements 820, then the nonconformance management algorithm 825 decides that changes are not needed. In either case, at step 920, the nonconformance management algorithm 825 adds this event to the event database 120.

If the nonconformance action planner 830 is notified that some action must be taken, a decision must be made to correct the nonconformance issue. The nonconformance action planner 830 will either invoke a pump programming change, at step 912, or schedule and appointment or notify the patient, at step 913, that a non-programming change should be made. In the above example, a pump programming change made by the nonconformance action planner 830 may be to increase the flow rate through pump reprogramming.

In the event that the nonconformance action planner 830 decides that a nonprogramming change may be needed, at step 913, the patient must be seen in order to continue the diagnostics and accomplish the nonprogramming change. In the above example, if the pump pressure remains high, it is possible that the catheter is kinked and the therapy of drug infusion has been stopped. In this case, it may not be possible to depend on pump reprogramming to restart the drug flow. It may require surgical intervention, but as a minimum, it would require that the patient with the pump 105 be seen by knowledgeable clinical personnel in order to take action to restart the therapy.

Nonprogramming changes 915, such as accessing the catheter access port with the syringe in order to aspirate the clot may be a viable solution. In either case, of pump programming changes or non programming changes, the path and the process is recorded in the database 120 at step 920. Preferably in all cases, payment is made subsequent to payment request at step 925.

An example of pump non-conformance is the implantable device current drain, or the current supplied by the implantable device battery. The amount of pump motor current drain could be monitored by sensors 750 within the implantable pump 105, which are then provided to the nonconformance management module 115. The total circuit current drain and the motor current drain are both expected to be within known limits during the life of the pump. If either of the current drains is outside of the range of expected values, then it is likely that something is not conforming to expectations within the pump 105. For example, the pump motor coil may have shorted turns in such a way as to increase the current drain from the battery during each current pulse to the pump. This would indicate that some mechanism of failure is occurring in the pump motor coil and coil is out of conformance or may have a failure mode.

In a similar way, if the electronic circuit current drain is outside of the normal limits it could indicate a failure in the electronic circuits. For example, if an integrated circuit or some interconnections between circuit components are shorted in some way, perhaps by contamination during the assembly process, the current drain might be excessive, which of course would diminish the expected life of the battery in the pump. In addition, the circuits may not be operating as designed, which could affect the therapy that's provided by the pump.

Thus, the pump performance acquisition instructions 810 may provide that the current drains be continuously sampled or measured in the pump 105 in various places in such a way as to compare these current drains to the established normal current drains. If the current drains measured were substantially outside of the normal range, a non-conformance message would be stored and sent by the pump 105 to the nonconformance management module 115. The normal range of currents could be either stored as part of the pump manufacturer requirements 825 within the pump, in the external device 110 (as preferred), or in a central repository of such data such as database 120. In any case, the current drains are compared to the expected range of the current drains, the expected range being provided by the manufacturer of the implanted pump.

Another possibility of non-conformance in the pump is an elevation of the relative humidity in the pump. A humidity sensor 750 could be in the pump 105 where the drug fluid flow path passes through. Excessive humidity has the potential to detrimentally affect the pump motor performance as well as the electronic circuit performance. Increasing pump humidity is possible by virtue of water vapor diffusing through the fluid flow path in the pump, and the water vapor accumulating in the pump assembly. The humidity sensor would be continuously exposed to the relative humidity and could be continuously or intermittently sampled or measured indicating the relative humidity in the pump. If the humidity exceeds the normal established limits by the manufacturer, it would be determined to be non-conforming.

A list of other possibilities of non-conformance include the pump outlet pressure, pump reservoir pressure, propellant pressure, and other physiologic sensors and their output levels. If the pump outlet pressure is excessive it may mean that there is an occlusion somewhere in the fluid path, which would indicate that the pumping mechanism is not causing fluid to flow normally, and of course then therapy might be unsatisfactory. Excessive pressure may indicate the catheter is occluded and fluid flow is diminished or zero.

It will be appreciated that the present invention may be implemented using other embodiments. Those skilled in the art recognize that the preferred embodiments may be altered and modified without departing from the true spirit and scope of the invention as defined in the appended claims.

I claim:

1. A system for providing treatment therapy to a patient comprising in combination:
   (a) an implantable drug delivery device comprising:
      (i) a housing;
      (ii) at least one drug reservoir within the housing and each configured to contain at least one drug;
      (iii) a flow control module configured to control a flow of drug from the drug reservoir through an infusion port;
      (iv) electronics coupled to the flow control module and configured to adjust the flow of drug with the flow control module;

(v) a telemetry module coupled to the electronics and configured to provide bi-directional communication between the delivery device and an external programmer; and (vi) a nonconformance monitor module coupled to the electronics, the nonconformance monitor module configured to monitor a pump outlet pressure and to generate pump performance data that includes the pump outlet pressure; and (b) an external programmer comprising:

(i) a memory having stored therein pump performance acquisition instructions;

(ii) a telemetry module configured to provide bi-directional communication between the external programmer and the implantable drug delivery device and to provide the pump performance acquisition instructions to the implantable drug delivery device and configured to receive pump performance data from the implantable drug delivery device; and (iii) a nonconformance management module stored in the memory, the nonconformance management module configured to determine whether the pump is conforming to performance requirements, based upon the pump performance data from the nonconformance monitor module, and to determine what action should be taken if non-conformance is determined.

2. The system of claim 1, further comprising:

(c) at least one server located at an entity selected from the group consisting of an insurance provider, a pharmacy, a hospital, a caregiver, a physician, and a device manufacturer; and (d) a computing network coupling the external programmer to the at least one server.

3. The system of claim 1, wherein the memory of the external programmer further includes patient performance requirements information.

4. The system of claim 1, wherein the memory of the external programmer further includes pump manufacturer requirements information associated with pump outlet pressure values.

5. The system of claim 1, wherein the memory of the external programmer further includes a scheduling module for scheduling an appointment to perform a non-programming change.

6. The system of claim 5, wherein the scheduling module is capable of contacting at least one entity for the appointment, wherein the entity is selected from the group consisting of a pharmacy, a caregiver, a hospital, and the patient.

7. An implantable drug delivery device having performance data reporting capability comprising in combination:

(a) a housing;

(b) a drug reservoir carried in the housing configured to contain at least one drug;

(c) a flow control module coupled to the drug reservoir for controlling the flow of the drug from the drug reservoir through an infusion port;

(d) electronics coupled to the flow control and a power source;

(e) a telemetry module coupled to the electronics;

(f) a memory coupled to the electronics, the memory containing pump performance acquisition instructions;

(g) at least one monitoring module coupled to the memory and the electronics that is configured to monitor at least one pump operation variable according to the pump performance acquisition instructions to produce performance data, wherein the performance data is stored in the memory;

(h) a non-conformance management module configured to retrieve the performance data from memory and to determine whether the pump is conforming to performance requirements and to further determine what action should be taken if non-conformance is determined; and (i) at least one reporting module coupled to the memory and the electronics, the reporting module configured to activate the telemetry module to report the performance data.

8. The implantable drug delivery device of claim 7, wherein the non-conformance management module is further configured to determine whether the pump performance data is indicative of a need for a non-programming change to the implantable drug delivery device.

9. The implantable drug delivery device of claim 7, wherein the non-conformance management module is further configured to determine whether the pump performance data is indicative of a programming change to the implantable drug delivery device.

10. The implantable drug delivery device of claim 7, wherein the pump performance data is selected from the group consisting of fluid outlet pressure, battery current drain, motor current drain, motor drive current profile, pump humidity and battery voltage.

11. The implantable drug delivery device of claim 7, wherein the non-conformance management module is configured to report the pump performance data to an external device through the telemetry module.

12. The implantable drug delivery device of claim 7, wherein the performance data includes at least one selection from the group consisting of pump humidity and pump outlet pressure.

13. The system of claim 1, wherein the pump performance data further includes data corresponding to at least one selected from the group consisting of battery current drain, motor current drain and motor drive current profile.

14. The implantable drug delivery device of claim 8, wherein the non-conformance management module is further configured to initiate the non-programming change to the implantable drug delivery device.

15. The implantable drug delivery device of claim 9, wherein the non-conformance management module is further configured to perform the programming change to the implantable drug delivery device.

* * * * *